United States Patent [19]

Labriola, II et al.

[11] Patent Number: 5,666,048

[45] Date of Patent: Sep. 9, 1997

[54] TECHNIQUE AND APPARATUS FOR MEASURING A DIRECT CURRENT FLOWING THROUGH A CONDUCTOR AT HIGH VOLTAGE

[75] Inventors: Donald P. Labriola, II, La Verne; John R. Fassett, Irvine, both of Calif.

[73] Assignee: Beckman Instruments, Inc., Fullerton, Calif.

[21] Appl. No.: 494,477

[22] Filed: Jun. 26, 1995

[51] Int. Cl.⁶ ............................................. G01R 19/18
[52] U.S. Cl. ............................ 324/120; 324/96; 204/452
[58] Field of Search ........................... 324/96, 120, 122, 324/133; 204/452, 453, 455, 602, 604, 605

[56] References Cited

U.S. PATENT DOCUMENTS

| | | | |
|---|---|---|---|
| 4,209,743 | 6/1980 | Muller et al. | 324/96 |
| 4,630,218 | 12/1986 | Hurley | 364/481 |
| 4,909,919 | 3/1990 | Morris et al. | 204/603 |
| 5,286,356 | 2/1994 | Jones et al. | 204/452 |
| 5,324,398 | 6/1994 | Erickson et al. | 205/701 |
| 5,342,497 | 8/1994 | Cathel et al. | 204/607 |
| 5,516,698 | 5/1996 | Begg et al. | 436/89 |

Primary Examiner—Kenneth A. Wieder
Assistant Examiner—Russell M. Kobert
Attorney, Agent, or Firm—William H. May; Janis C. Henry

[57] ABSTRACT

A technique and circuit for measuring direct current flowing through a conductor at a high voltage employs a capacitor connected in series with the conductor, and a neon lamp connected in parallel with the capacitor. The series connected capacitor and conductor are connected to a high voltage source such that the current flowing through the series connected capacitor and conductor charges up the capacitor. Since the capacitor and the neon lamp are connected in parallel, the voltage across the electrodes of the neon lamp follows the voltage across the capacitor. When the voltage across the electrodes of the neon lamp reaches the lamp's ignition voltage, the neon lamp fires, and discharges the capacitor until the voltage across the electrodes of the neon lamp falls to the lamp's extinction voltage. The light signal generated by the neon lamp is picked up by a fiber optic cable and transmitted to a remote receiver for processing. The direct current flowing through the conductor may then be calculated by the remote receiver from the frequency of the transmitted light signal, or a qualitative indication of the current may be made through visual observation of the lamp's intensity.

10 Claims, 5 Drawing Sheets

TECHNIQUE AND APPARATUS FOR MEASURING A DIRECT CURRENT FLOWING THROUGH A CONDUCTOR AT HIGH VOLTAGE

BACKGROUND OF THE INVENTION

This invention relates in general to electrical current measuring techniques and apparatuses and in particular, to a high voltage, direct current measuring technique and apparatus.

In certain applications, it is desirable to measure a direct current flowing through a conductor at a high voltage. For example, in a multi-capillary electrophoresis system it is desired to know the current in each of a multitude of capillaries electrically connected together in parallel. During the chemical electrophoresis operation, one end of each capillary is immersed in a common pool of conductive liquid or gel buffer along with an electrode connected to electrical ground, while the other end is immersed in a vial of buffer along with an electrode maintained at a high dc voltage, either positive or negative. Typically, such voltages may be in a range of 5,000 to 50,000 volts, while the current flowing through each of the capillaries may range between 1 to 100 microamps.

One technique for measuring current flowing through a conductor is to measure a voltage across a known resistance connected in series with the conductor, and calculate the current from the measured voltage and known resistance using Ohm's law. For digital processing and/or display purposes, it is desirable to digitize the measured analog voltage using an analog-to-digital converter. When doing so, the measured analog voltage is generally first scaled with respect to the full-scale range of the analog-to-digital converter to improve the accuracy of the conversion. Examples of such full-scale ranges are 0 to 5 volts, and 0 to 10 volts.

In a multi-capillary electrophoresis system, however, it is often impractical to measure a voltage across a known resistance at the electrical ground end of the capillaries since that end is immersed in a common pool of conductive liquid or gel buffer. Also, it is often impractical to measure a voltage across a known resistance at the high voltage end, because of the large voltage conversion or level shifting (e.g., up to 50,000 volts) required to scale the measured analog voltage down to the full-scale voltage range of a typical analog-to-digital converter (e.g., 0 to 5, or 0 to 10 volts).

OBJECTS AND SUMMARY OF THE INVENTION

Accordingly, general objects of the present invention are an improved method and an improved apparatus for measuring a direct current flowing through a conductor at a high voltage, which method and apparatus are suitable for such applications as in a multi-capillary electrophoresis system.

In particular, the method and apparatus preferably measures such direct current in a manner overcoming the previously described problems associated with the conventional "voltage-across-a-resistor" technique when used in such applications as in a multi-capillary electrophoresis system.

These and additional objects are accomplished by the various aspects of the present invention, wherein briefly stated, one aspect of the present invention is a method of determining the magnitude of a direct current comprising: providing the direct current to a capacitor such that a voltage across the capacitor builds up substantially proportionally to an integral of the direct current; discharging the voltage across the capacitor to a minimum voltage each time the voltage across the capacitor builds up to a maximum voltage; and determining the magnitude of the direct current from the frequency of the building up and discharging of the voltage across the capacitor.

In the preferred embodiment, the repetitive building up and discharging of the voltage across the capacitor is detected by measuring the frequency of a light signal generated by a light emitting device, wherein the light emitting device is connected to the capacitor such that the light emitting device emits a flash of light for each time the capacitor discharges. The direct current can then be calculated from the known minimum and maximum voltages associated with the discharging of the capacitor, and the measured frequency resulting from such repetitive building up and discharging of charge on the capacitor.

Another aspect of the present invention is an apparatus for determining the magnitude of a direct current. Included in the apparatus are a capacitor receiving the direct current; means connected to the capacitor, for allowing a voltage across the capacitor to repetitively build up substantially according to an integral of the direct current and discharge back to a minimum voltage when the capacitor voltage reaches a maximum voltage; means for generating a signal responsive to the voltage across the capacitor; and means receiving the signal responsive to the voltage across the capacitor, for determining the magnitude of the direct current from a frequency on the signal indicative of the repetitive building up and discharging of the capacitor voltage.

Another aspect of the present invention is a method of detecting a defective capillary in an electrophoresis system having a plurality of capillaries, comprising: connecting individual capacitors in series to corresponding ones of the plurality of capillaries; connecting the series connected individual capacitors and corresponding ones of the plurality of capillaries to a high voltage power supply; connecting individual light sources to corresponding ones of the individual capacitors such that the individual light sources emit light for each time a voltage across corresponding ones of the individual capacitors reaches a predetermined value; and detecting a defective capillary from the intensity of the light emanating from the individual light sources.

Another aspect of the present invention is a method for electrophoretic separation of a sample, comprising passing a direct electrical current through a separation channel containing the sample and an electrolyte to cause the sample to separate; providing the direct current to a capacitor to charge the capacitor and causing it to discharge when voltage across the capacitor reaches a maximum voltage; and determining the magnitude of the direct current.

Yet another aspect of the present invention is an apparatus for electrophoretic separation of a sample, comprising means for passing a direct electrical current through a separation channel containing the sample and an electrolyte to cause the sample to separate; a capacitor receiving the direct current; means for causing the capacitor to discharge when voltage across the capacitor reaches a maximum voltage; and means for determining the magnitude of the direct current.

Additional objects, features and advantages of the various aspects of the present invention will be apparent from the following description of its preferred embodiments, which description should be taken in conjunction with the accompanying drawings.

DETAILED DESCRIPTION OF THE PREFERRED EMBODIMENT

Figure 1:
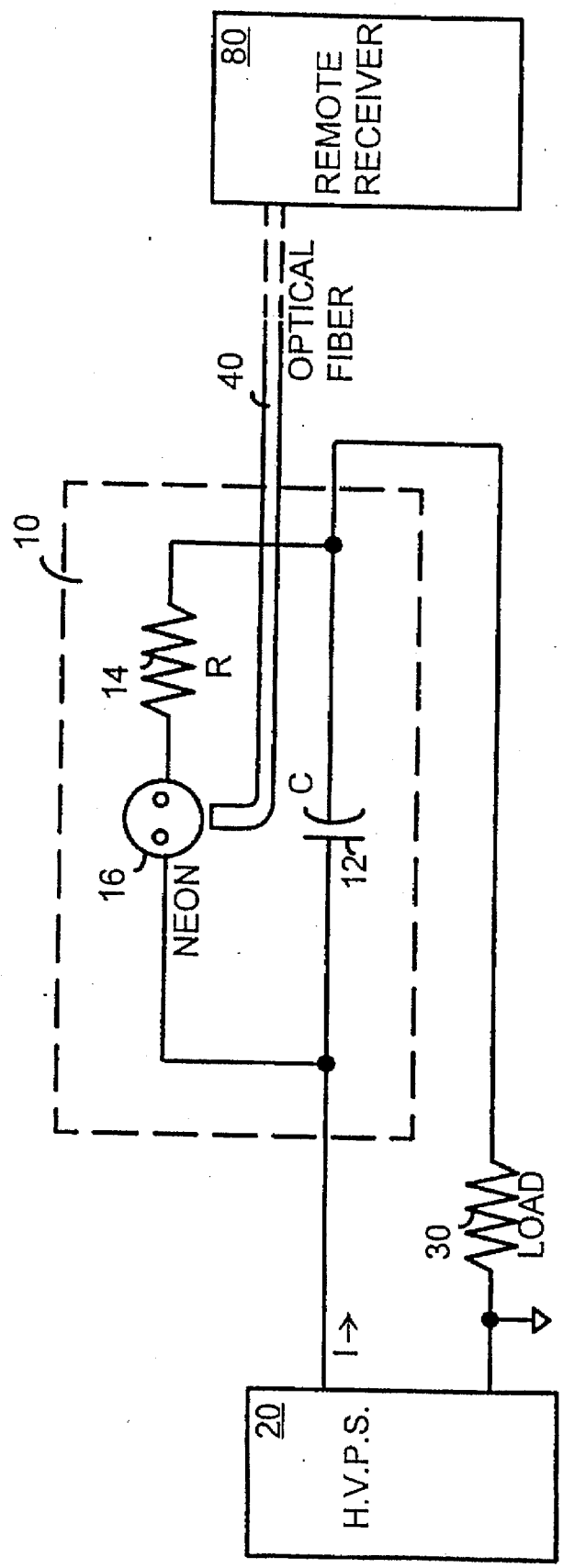
FIG. 1 illustrates, as an example, a circuit utilizing aspects of the present invention for measuring a direct current resulting from a high voltage power supply being connected to a load resistance.

FIG. 1 illustrates a circuit 10 useful for measuring a direct current ("I") drawn by a load resistor 30 ("LOAD") from a high voltage power supply 20 ("H.V.P.S."). Included in the circuit 10 are a capacitor 12 (having a capacitance value "C"), a current limiting resistor 14 (having a resistance value "R"), and a neon lamp 16 ("NEON"). The current limiting resistor 14 and neon lamp 16 are connected together in series, and this combination is in turn, connected in parallel to the capacitor 12.

The neon lamp 16 performs the function of a voltage-controlled switch. When a voltage $V_{neon}$ across the electrodes of the neon lamp 16 is between an extinction voltage $V_{ex}$ and ignition voltage $V_{ig}$ associated with the neon lamp 16, the neon lamp 16 does not fire (i.e., does not emit light). In this condition, the neon lamp 16 functions like an "open switch", being characterized by a very high resistance and very low leakage current. When the voltage $V_{neon}$ becomes equal to or greater than the ignition voltage $V_{ig}$ associated with the neon lamp 16, however, the neon lamp 16 fires (i.e., emits light). In this condition, the neon lamp 16 functions like a "closed switch", being characterized by a low resistance and relatively high current.

With the circuit 10 connected in series with the load resistor 30 between positive and negative inputs of the high voltage power supply 20, a voltage $V_{cap}$ builds up across the capacitor 12 according to the following well known equation, $$V_{cap} = \frac{1}{C} \int I \, dt \quad (1)$$

until the voltage $V_{neon}$ across the electrodes of the neon lamp 16 rises to the ignition voltage $V_{ig}$ associated with the neon lamp 16, at which time, the neon lamp 16 fires (i.e., functions as a "closed switch"), discharging the voltage $V_{cap}$ through the current limiting resistor 14 and the neon lamp 16, until the voltage $V_{neon}$ across the electrodes of the neon lamp 16 falls to the extinction voltage $V_{ex}$ associated with the neon lamp 16, at which time, the neon lamp 16 extinguishes (i.e., functions as an "open switch") and the voltage $V_{cap}$ again builds up across the capacitor 12 according to equation (1). Thus, repetitive cycles of the voltages $V_{neon}$ and $V_{cap}$ building up and discharging occur as shown, for example, in FIG. 3A, wherein the waveforms for $V_{neon}$ and $V_{cap}$ are substantially identical (except for a small voltage drop across the current limiting resistor 14).

Figure 3A:
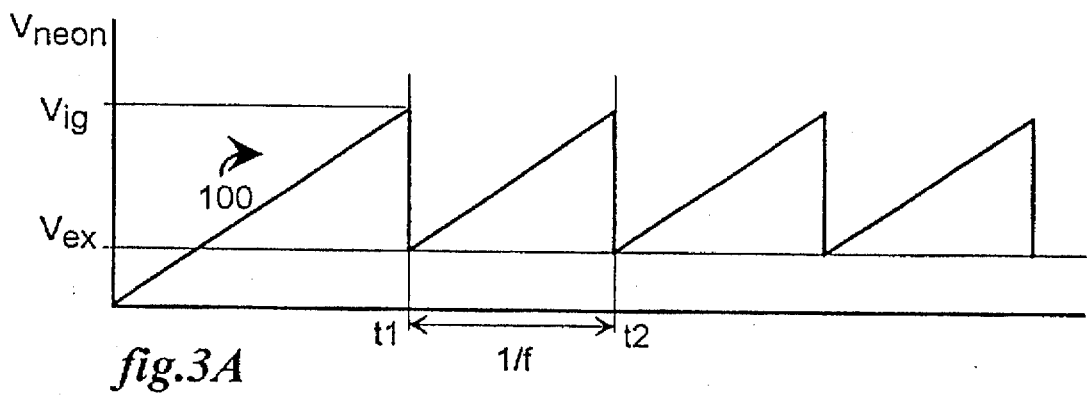
FIGS. 3A-3D respectively illustrate, as examples, waveforms of a voltage $V_{neon}$ and current $I_{neon}$ associated with a neon lamp in a circuit such as depicted in FIG. 1; a current $I_{cap}$ flowing to and from a corresponding capacitor in a circuit such as depicted in FIG. 1; and a voltage $V_{cpl}$ across a corresponding capillary connected to a circuit such as depicted in FIG. 1.

As a result, the neon lamp 16 generates a series or train of light pulses having the same frequency ("f") as the repetitive cycles of the voltage $V_{cap}$ building up and discharging across the capacitor 12, wherein preferably, the duration of the discharge time is much shorter than the charging time, as shown, for example in FIG. 3A. For a load resistor 30 having a resistance typical for a multi-capillary electrophoresis system, capacitance values of 0.001 μF to 0.1 μF on the capacitor 12 and resistance values of 100 Ω to 1000 Ω on the current limiting resistor 14, result in such a preferred relationship.

The train of light pulses (also referred to herein as "the light signal") generated by the neon lamp 16 may then be captured and transmitted, for example, through a fiber optic cable 40 of suitable type and wavelength, to a remote receiver 80 having a light detector (not shown) which converts the received light signal into an electrical signal in a range generally compatible with the full-scale ranges of typical analog-to-digital converters (e.g., 0 to 5 volts). Thus, the fiber optic cable 40 effectively eliminates the voltage conversion or translation problem of the prior art voltage-across-a-resistor technique. In particular, it conveys information from one of its ends in the high voltage section of the circuit 10 (e.g., up to 50,000 volts), to its other end which is connected to a light detector outputting at near ground potential (e.g., 0 to 5 volts).

The fiber optic cable 40 is preferably comprised of a non-conductive fiber or glass material to eliminate any potential high voltage arcing problem. To effectively and/or efficiently couple the fiber optic cable 40 to the neon lamp 16, it is also preferable to focus the neon lamp 16 output onto an end of the fiber optic cable 40, as depicted, for example, in FIG. 1.

The remote receiver 80 preferably includes a processing unit (not shown) for processing the electrical signal generated by its light detector (not shown), and either a device (not shown) for directly measuring the frequency of the electrical signal generated by the light detector or a frequency-to-voltage conversion device (not shown) for indirectly measuring it by first converting the frequency to a voltage, then measuring the voltage to determine the frequency, wherein all such components of the remote receiver 80 are conventional components having well known constructions and operations. Since the electrical signal generated by the light detector is derived from the transmitted light signal of the neon lamp 16, which has the same frequency ("f") as the repetitive cycles of the voltage $V_{cap}$ building up and discharging across the capacitor 12, the electrical signal generated by the light detector also has that same frequency.

An approximation for the magnitude of the direct current "I" can then be calculated by the processing unit (not shown) of the remote receiver 80 from the directly or indirectly measured frequency of the light signal generated by the light detector (not shown) of the remote receiver 80 from the following equation:

$$I \approx C(V_{ig} - V_{ex})f \quad (2)$$

where:

C = capacitance of capacitor 12;

$V_{ig}$ = ignition voltage of neon lamp 16;

$V_{ex}$=extinction voltage of neon lamp 16; and f=frequency of the repetitive cycles of the voltage $V_{cap}$ building up and discharging across the capacitor 12.

Figure 2:
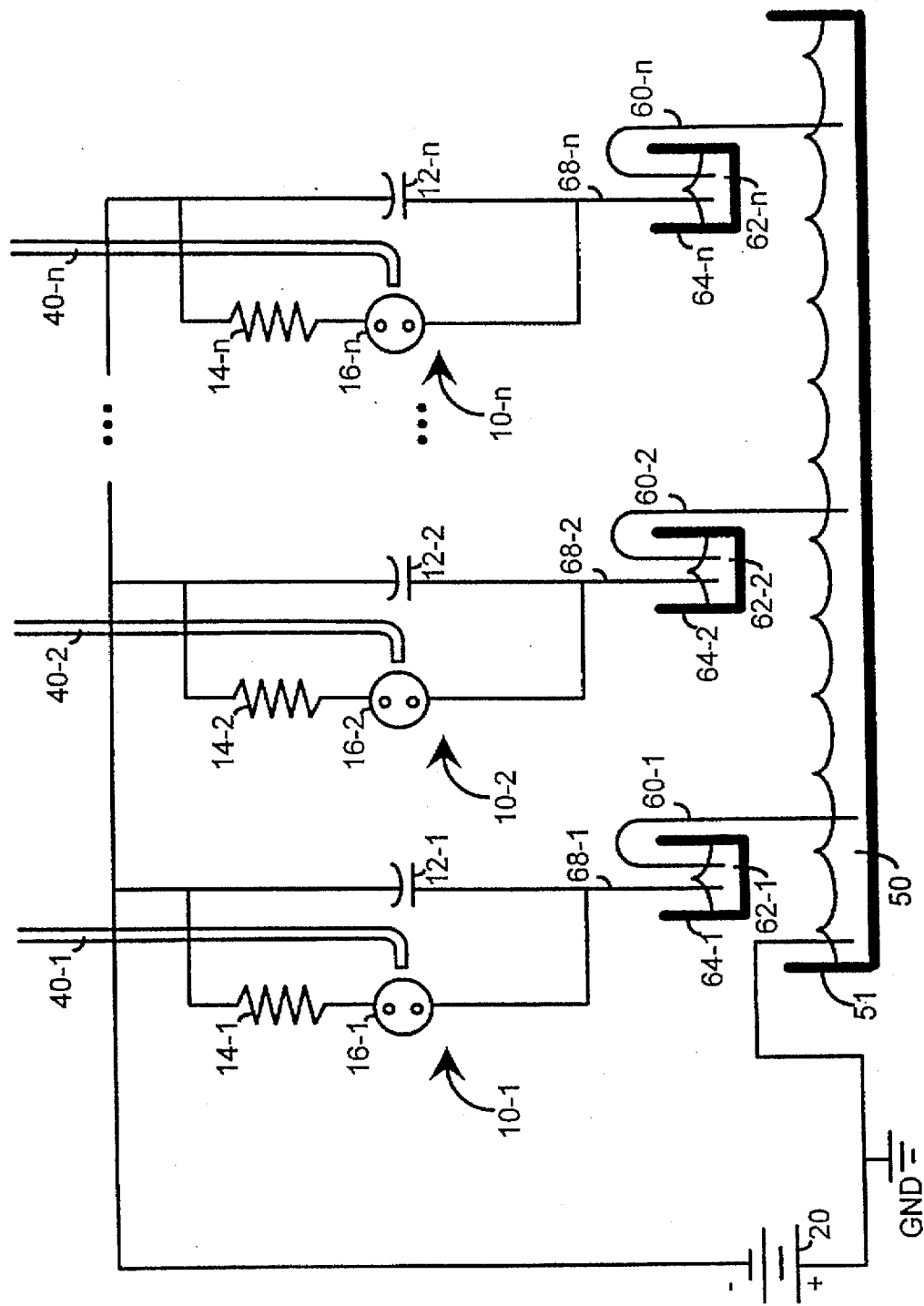
FIG. 2 illustrates, as an example, a multi-capillary electrophoresis system employing the circuit of FIG. 1, utilizing aspects of the present invention.

FIG. 2 illustrates, as an example, a multi-capillary electrophoresis system employing the circuit of FIG. 1. In this system, the "+" (i.e., positive) side of the high voltage power supply 20 is grounded. Current flow is from the "+" side of the high voltage power supply 20 into buffer 50 contained in a common buffer pool 51, thence into the capillaries 60-1 to 60-n, thence into vials 64-1 to 64-n respectively containing buffer 62-1 to 62-n and respectively corresponding to capillaries 60-1 to 60-n, thence into electrodes 68-1 to 68-n respectively corresponding to vials 64-1 to 64-n, thence into measuring circuits 10-1 to 10-n individually constructed similarly to circuit 10 of FIG. 1, and thence back to the "−" (i.e., negative) side of the high voltage power supply 20. Fiber optic cables 40-1 to 40-n respectively corresponding to measuring circuits 10-1 to 10-n capture and transmit light signals from their corresponding neon lamps 16-1 to 16-n, to one or more remote processors (not shown) for calculating the magnitudes of the direct currents flowing through their respective capillaries 60-1 to 60-n according to equation (2) above.

The neon lamps, 16-1 to 16-n, although located in the high-voltage section of the circuitry, may be positioned such that they can be viewed directly by a user. If the current in any one of the capillaries, 60-1 to 60-n, is somewhat less than in the remaining capillaries, the corresponding lamp in the array of neon lamps, 16-1 to 16-n, will appear to be dimmer than the rest (i.e., have a lower light intensity), providing an immediate visual indication to the user that there is a problem with that capillary. Such an immediate visual indication of a defective capillary can be particularly useful in practice.

Figure 3B:
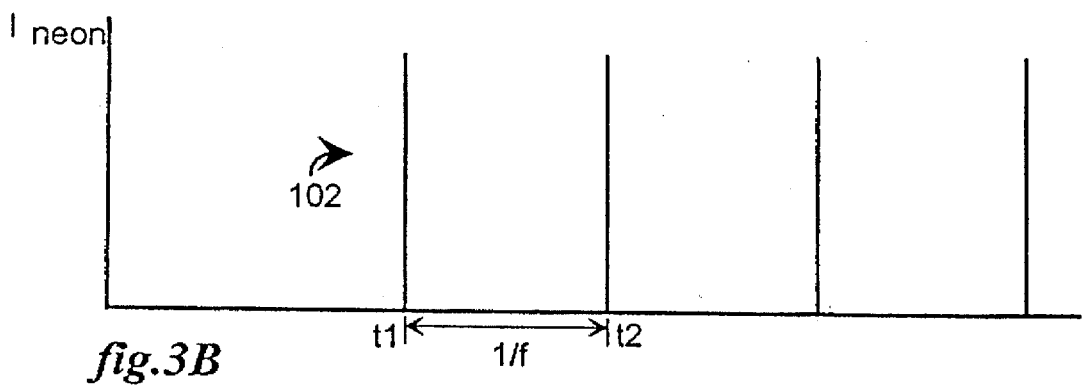
Figure 3C:
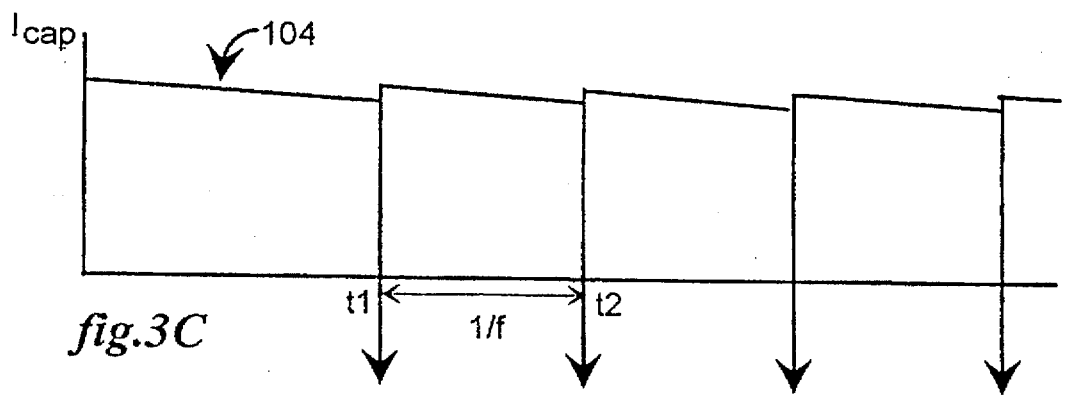
Figure 3D:
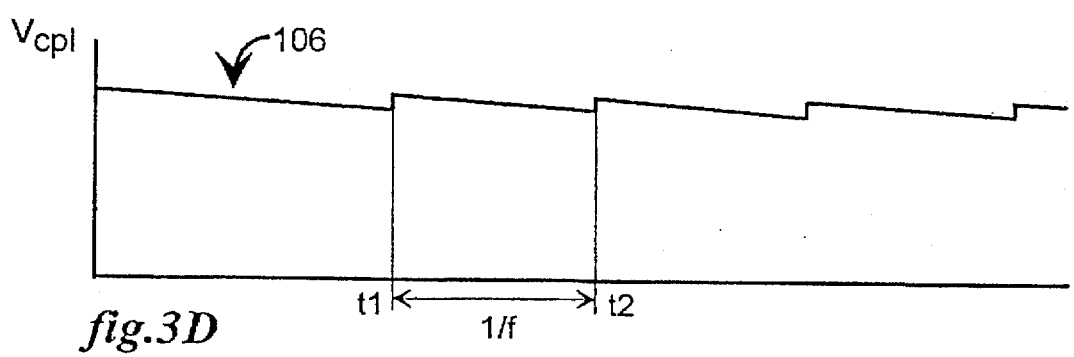

FIGS. 3A–3D respectively illustrate waveforms of a voltage $V_{neon}$ and current $I_{neon}$ associated with one of the neon lamps, 16-1 to 16-n, a current $I_{cap}$ flowing to and from a corresponding one of the capacitors, 12-1 to 12-n, and a voltage $V_{cpi}$ across a corresponding one of the capillaries, 60-1 to 60-n. As shown in FIG. 3B, the current $I_{neon}$ flowing through a neon lamp is substantially negligible until the neon lamp fires at time t1, for example. For a multi-capillary system such as depicted in FIG. 2, the current $I_{neon}$ flowing through a neon lamp may appear as a train of pulses 102 having, for example, a pulse width of $10^{-5}$ seconds, a pulse amplitude of $10^{-2}$ amperes, and a pulse frequency "f" of 10 to 1000 Hertz. As shown in FIG. 3C, the corresponding current $I_{cap}$ flowing to and from a capacitor may appear as being substantially constant at a magnitude determined by the load resistance and the high voltage power supply, until its corresponding neon lamp fires at time t1, for example, at which time, the capacitor discharges, generating a current flowing in the opposite direction. For a multi-capillary system such as depicted in FIG. 2, the current $I_{cap}$ flowing to and from a capacitor may appear as signal 104 having a substantially constant value, for example, of $10^{-5}$ amperes with periodic pulses having a magnitude of $10^{-2}$ amperes. As shown in FIG. 3D, the corresponding voltage $V_{cpi}$ across a capillary appears substantially constant except for a ripple effect caused by the neon lamp voltage rising and falling between its extinction voltage $V_{ex}$ and its extinction voltage $V_{ig}$. Since these voltages are typically around 50 to 80 volts, and the high power voltage supply supplies voltages to a multi-capillary system such as depicted in FIG. 2, around 5,000 to 50,000 volts, the magnitude of the ripple may be as small as 0.01%, for example, or as large as 1.6%, for these types of systems.

Figure 4:
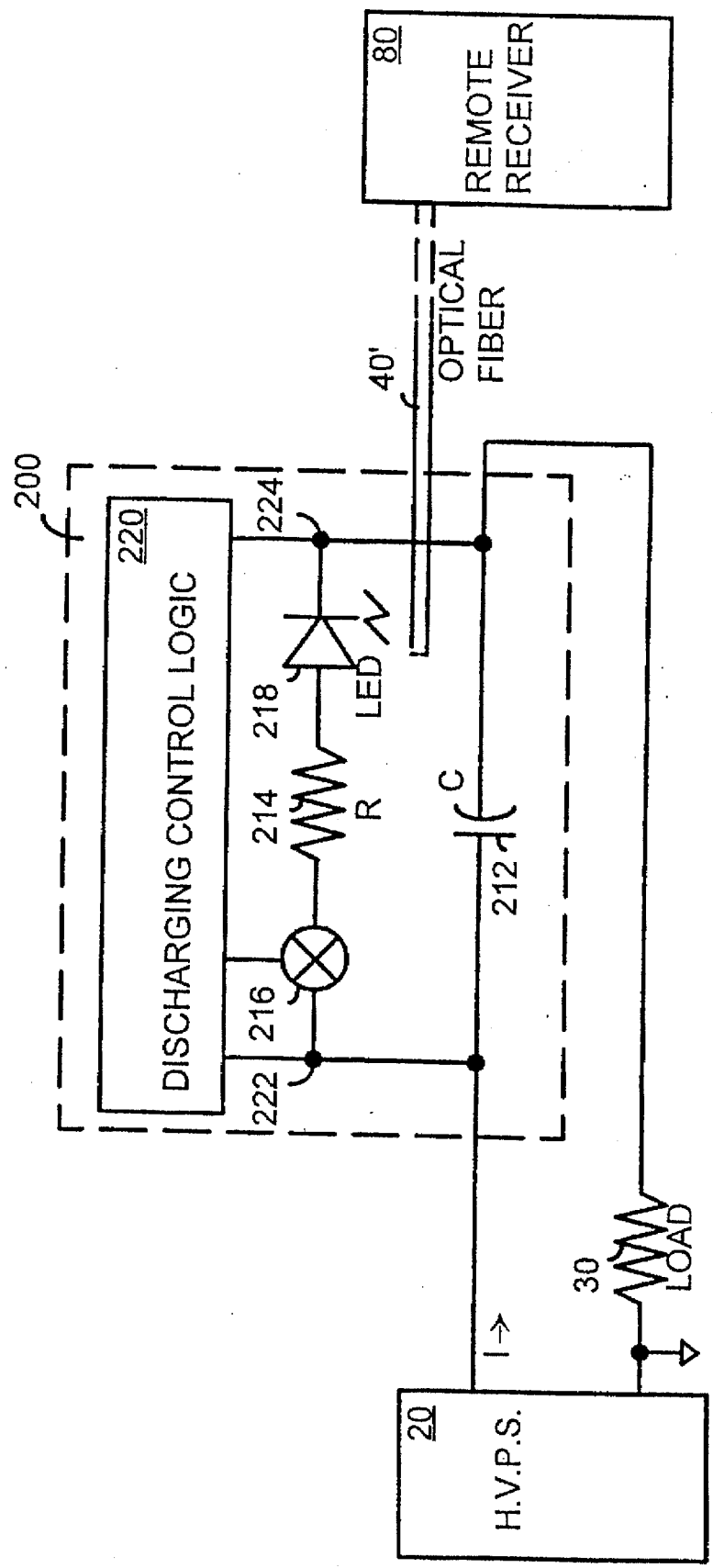
FIG. 4 illustrates, as an example, an alternative circuit, utilizing aspects of the present invention, for measuring a direct current resulting from a high voltage power supply being connected to a load resistance.

FIG. 4 illustrates, as an example, an alternative circuit 200 useful for measuring a direct current "I" drawn by a load resistance 30 from a high voltage power supply 20. The circuit 200 is particularly useful in certain applications where the magnitude of a ripple on a voltage measured across the load resistance 30 (for example, $V_{cpi}$, for the multi-capillary system of FIG. 2) may be excessive due to the high ignition and extinction voltages, $V_{ig}$ and $V_{ex}$, of the neon lamp 16 when measuring a current flowing through the load resistance 30 with the circuit 10 of FIG. 1. In the circuit 200, the neon lamp 16 of the circuit 10 in FIG. 1, is replaced by an analog switch 216, a discharging control logic circuit 220, and a light emitting diode ("LED") 218. The analog switch 216 is "open" while the capacitor 212 is charging up to a maximum voltage $V_{max}$, and "closes" when the voltage $V_{cap}$ on the capacitor 212 reaches $V_{max}$. Since the resistance "R" of a current limiting resistor 214 is very small, when the analog switch 216 closes, the capacitor 212 discharges through the analog switch 216, current limiting resistor 214, and light emitting diode 218. The light emitting diode 218 then emits a flash of light for each such discharging of the capacitor 212, which light is picked up and transmitted to a remote receiver 80 via fiber optic cable 40', and processed in a similar fashion as described in reference to FIG. 1 for the neon lamp's light signal.

Figure 5:
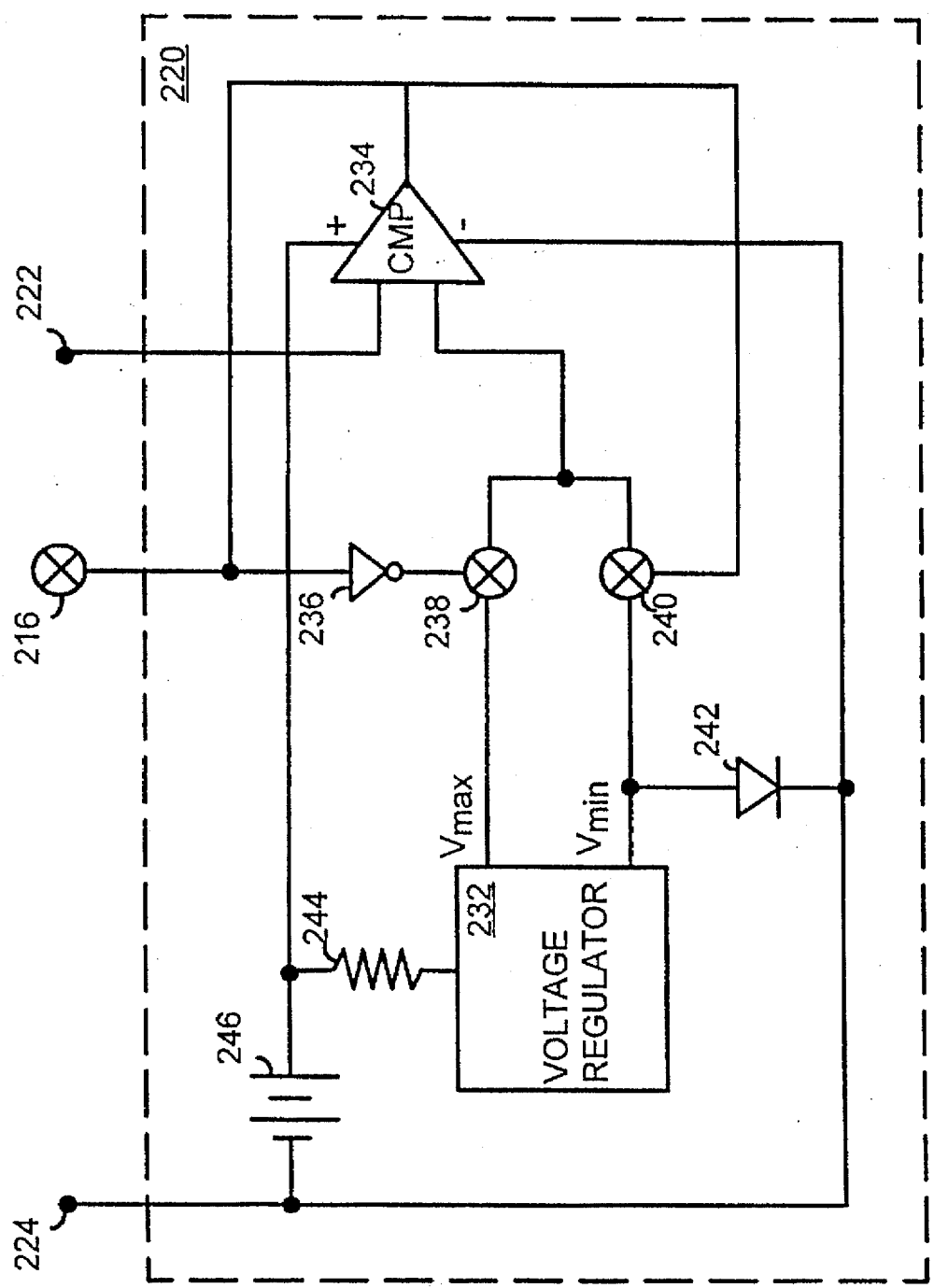
FIG. 5 illustrates, as an example, a circuit implementing the discharging control logic of the alternative circuit depicted in FIG. 4.

FIG. 5 illustrates, as an example, one implementation of the discharging control logic circuit 200 of FIG. 4. A voltage regulator 232 powered by a battery 246, provides two regulated voltages, $V_{max}$ and $V_{min}$, for use by a comparator 234. The output of the comparator 234 controls three analog switches (or passgates or transmission gates), 216, 238, and 240. Initially, the output of comparator 234 is LOW, turning off analog switches 216 and 240, and turning on, through inverter 236, analog switch 238. As a result, the comparator 234 compares the voltage $V_{max}$ provided by voltage regulator 232 against the voltage $V_{cap}$ across the capacitor 212, as picked off at node 222. When the voltage $V_{cap}$ across the capacitor 212 reaches or exceeds $V_{max}$, the output of the comparator 234 becomes HIGH, turning on analog switches 216 and 240, and turning off, through inverter 236, analog switch 238. As a result, as previously described, the capacitor 212 discharges causing the light emitting diode 218 to emit a flash of light. The comparator 234 then compares the voltage $V_{min}$ provided by voltage regulator 232 against the voltage $V_{cap}$ across the capacitor 212, as picked off at node 222. When the voltage $V_{cap}$ becomes less than or equal to $V_{min}$, the output of the comparator 234 once again goes LOW, turning off analog switches 216 and 240, and turning on, through inverter 236, analog switch 238. The cycle then repeats, generating a light emitting diode current signal similar to that of the neon lamp signal 102 depicted in FIG. 3B.

The above-described system for measuring the magnitude of a direct current is particularly advantageous in the context of multi-channel electrophoretic separations. In capillary electrophoretic separation systems, voltages of the order of tens of thousands of volts are applied across the separation channel after a sample to be separated has been introduced into the separation channel. The presence of such a high voltage makes it hazardous for an operator of the system. The conventional way of measuring current in the electrophoretic channel is to perform the measurement at or near ground potential. In certain multi-capillary capillary electrophoretic applications such as that shown in FIG. 2, however, this may not be practical since all capillaries are immersed in a common pool of buffer at ground potential. On the other hand, performing the measurements at high voltage ends of the capillaries may be hazardous to the operator.

The above-described system for measuring direct current can be performed at high voltage with minimal hazard to the operator. This is due to the fact that the direct current measurement is converted to an optical signal and non-electrically conductive means such as a fiberoptic cable may be used to communicate the optical signal to a measurement device for measuring the frequency of the charging and discharging of the capacitor. In reference to FIG. 2, for example, samples to be separated and analyzed are first introduced into separation channels such as capillaries 60-1, 60-2, . . . , 60-n (or other channels known to those skilled in the art). A direct electrical current is then passed through the capillaries by means of a voltage supply 20 and electrolytes 50, 62-1, 62-2, . . . , 62-n. Using the system of the invention described above, the current through each of the capillaries can be determined. In a multi-capillary electrophoretic system, it is useful to measure the current in each of the capillaries connected electrically in parallel.

Although the various aspects of the present invention have been described with respect to a preferred embodiment, it will be understood that the invention is entitled to full protection within the full scope of the appended claims.

What is claimed is:

1. An apparatus for electrophoretic separation of one or more samples, comprising:

a plurality of separation channels containing said sample (s) and an electrolyte;

voltage supply having a high voltage terminal and a low voltage terminal for passing direct electrical currents through the channels to cause the sample(s) to separate into components;

a plurality of capacitors, each capacitor connected between the high voltage terminal and a corresponding separation channel so that the direct current passing through each capacitor and its corresponding separation channel will charge such capacitor;

means for causing each of the capacitors to discharge when voltage across each of the capacitors reaches a maximum voltage; and means for determining the magnitudes of the direct currents.

2. The apparatus of claim 1, said causing means including a neon lamp.

3. The apparatus of claim 1, said determining means including a current limiting resistor.

4. The apparatus of claim 1, said causing means including a neon lamp, wherein said resistor is connected in series with the lamp.

5. The apparatus of claim 1, said determining means including means responsive to light emission from the lamp for determining frequency of discharge of the capacitor.

6. The apparatus of claim 1, further comprising an optical path for communicating the magnitude of the direct current.

7. The apparatus of claim 1, wherein said voltage supply passes direct currents of magnitude in the range of about 1 to 100 microamps to the separation channels.

8. The apparatus of claim 1, further comprising a buffer, said separation channels having two ends, wherein one end of each channel is in electrical contact with said buffer, said buffer being at a reference potential.

9. The apparatus of claim 1, said reference potential being substantially ground potential.

10. The apparatus of claim 1, said causing means including a gas discharge lamp.

* * * * *